US00PP17209P2

(12) United States Plant Patent
Korlipara

(10) Patent No.: US PP17,209 P2
(45) Date of Patent: Nov. 14, 2006

(54) ***ECHINACEA PURPUREA* PLANT NAMED 'FANCY FRILLS'**

(50) Latin Name: *Echinacea purpurea*
Varietal Denomination: Fancy Frills

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 45 days.

(21) Appl. No.: 11/155,225

(22) Filed: Jun. 16, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct cultivar of *Echinacea purpurea* plant named 'Fancy Frills' characterized by its unique frilled and doubled ray florets that are held out stiffly, reddish to maroon cones, lovely fragrance, and an upright vigorous habit.

1 Drawing Sheet

Botanical denomination: *Echinacea purpurea.*
Variety designation: 'Fancy Frills'.

The present invention relates to a new and distinct cultivar of *Echinacea purpurea* and given the name 'Fancy Frills'. *Echinacea* is in the family Asteraceae. This new cultivar originated as a seedling from an open pollinated cross between *Echinacea* 'Ruby Giant', an unpatented plant, as the seed parent and an unknown pollen parent.

This new *Echinacea purpurea* cultivar is distinguished by:

1. Large rose colored double and frilled florets.
2. Ray florets spread out stiffly, parallel to ground.
3. Reddish to maroon cones.
4. Lovely fragrance.
5. Strong upright stems.
6. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

The photograph shows a close up of the floret of a one year old *Echinacea purpurea* 'Fancy Frills' grown in the ground in the field in the summer in Canby, Oreg.

DETAILED PLANT DESCRIPTION

The following is a detailed description of the new *Echinacea purpurea* cultivar based on observations of a one-year-old specimen growing in the ground in full sun under typical outdoor conditions. Canby is in Zone 8 on the USDA Hardiness map. Temperatures range from a high of 95 degrees F. in August to 32 degrees F. in January. Normal rainfall in Canby is 42.8 inches per year in the trial fields in Canby, Oreg. The color descriptions are all based on The Royal Horticultural Society Colour Chart.

Botanical denomination: *Echinacea purpurea.*
Variety designation: 'Fancy Frills'.
Parentage: *Echinacea purpurea* 'Ruby Giant'×unknown.

Plant:
- *Type.*—Herbaceous perennial.
- *Hardiness.*—USDA Zones 4 to 9.
- *Size.*—30 cm wide and 74 cm tall to top of florets.
- *Form.*—Basal clump.
- *Vigor.*—Excellent.
- *Roots.*—Fibrous, with many downward growing and few laterals, ivory in color, Yellow White 158D. Roots develop easily from cuttings from the crown.

Stem:
- *Type.*—Ascending.
- *Size.*—50 cm tall to top of florets and 9 mm wide.
- *Internode length.*—5 to 7 cm.
- *Surface texture.*—Strigose.
- *Color.*—Yellow Green 145A on shaded side and Greyed Purple 187A to B on sun side.

Leaf:
- *Type.*—Simple.
- *Shape.*—Ovate.
- *Arrangement.*—Alternate.
- *Blade length.*—12.5 to 14 cm.
- *Width.*—7 to 8 cm at the widest part.
- *Margins.*—Coarsely serrate or toothed.
- *Apex.*—Acuminate.
- *Base.*—Obliquely attenuate, continuing down petiole.
- *Surface texture.*—Strigose.
- *Venation.*—Pinnate, with three main veins from near the base.
- *Color.*—Topside —Deep Green, Closest to Yellow Green 147A. Bottom — Yellow Green 147B.
- *Petiole size.*—6 cm long and 4 mm wide if basal leaf, 2 to 4 cm long and 4 mm wide if cauline leaf.
- *Petiole surface texture.*—Strigose.

*Petiole color.*—Yellow Green 145A with blotches of Greyed Purple 187A on both sides.

Inflorescence:

*Type.*—Long stalked terminal heads.

*Number of stalks in first flush.*—15 on average.

*Peduncle.*—Height: 11 to 19 cm. Diameter: 7 mm near floret head. Surface texture: Strigose. Color: Yellow Green 145A marked or mottled with Greyed Purple 187B.

Flower:

*Type.*—Perfect, zygomorphic.

*Size.*—11.5 cm wide and 2 to 4 cm deep as disc enlarges.

*Ray florets.*—In 4 series with prominent pleats or veins, presented at various angles. Shape: Most oblong with the tip two to three toothed, closest to the cone they may have a tooth or appendage that is linear to oblanceolate and curl up (12 mm long) giving the center frill, margins entire. Size: Grows to 4 cm long, 1.2 cm wide. Texture: Rubbery. Surface texture: Glabrous. Color: Ray floret, topside — Red Purple 64C at base to 64D at middle and Greyed Purple 186C at tip. Ray floret, bottom side — Closest to Greyed Purple 186B.

*Disc.*—Shape: Convex becoming conic. Size: 4.5 cm wide and becoming 3.5 cm deep with maturity. Color: Greyed Purple 185A when in bud, opening to red orange, Red Orange 34A overall.

*Disc floret.*—9 mm long, Yellow Green 144B, 5 lobed, each floret with one persistent, very stiff bract, 14 mm long, which gives the disc color. Bract color: Yellow Orange 22A when in bud, changing to orange, Yellow Orange 22A tipped with Greyed Purple 187A changing to Greyed Purple 187A and B.

*Pistil.*—7 mm long, extruding, 2-branched stigma, Greyed Purple 187A.

*Stamen number.*—5.

*Pollen color.*—Scant, Yellow Orange 20A.

*Phyllaries.*—Phyllaries in eight or more leafy series and continuing down the peduncle, lobes lanceolate in shape, reflexed, apex acuminate, strigose, area: 5 cm wide and 2.5 deep.

*Phyllary size.*—Grows to 25 mm long and 3 mm wide.

*Phyllary color.*—Yellow Green 147A.

*Bloom period.*—July through September in Canby, Oreg.

*Fragrance.*—Lovely, strong.

Seed: Not seen.

*Fertility.*—Fertile.

Disease and pests: *Echinacea* are susceptible to leaf miners, powdery mildew, bacterial spots, and gray mold. None of these have been observed on plants grown under commercial conditions in Canby, Oreg. This variety has no known resistance to normal *Echinacea* problems.

COMPARISONS TO SIMILAR *Echinacea*

Compared to *Echinacea purpurea* 'Ruby Giant', an unpatented plant and the seed parent, the ray florets of this new cultivar are in 4 or more series rather than 2 and the leaves are broader.

I claim:

1. A new and distinct cultivar of *Echinacea purpurea* plant as herein illustrated and described.

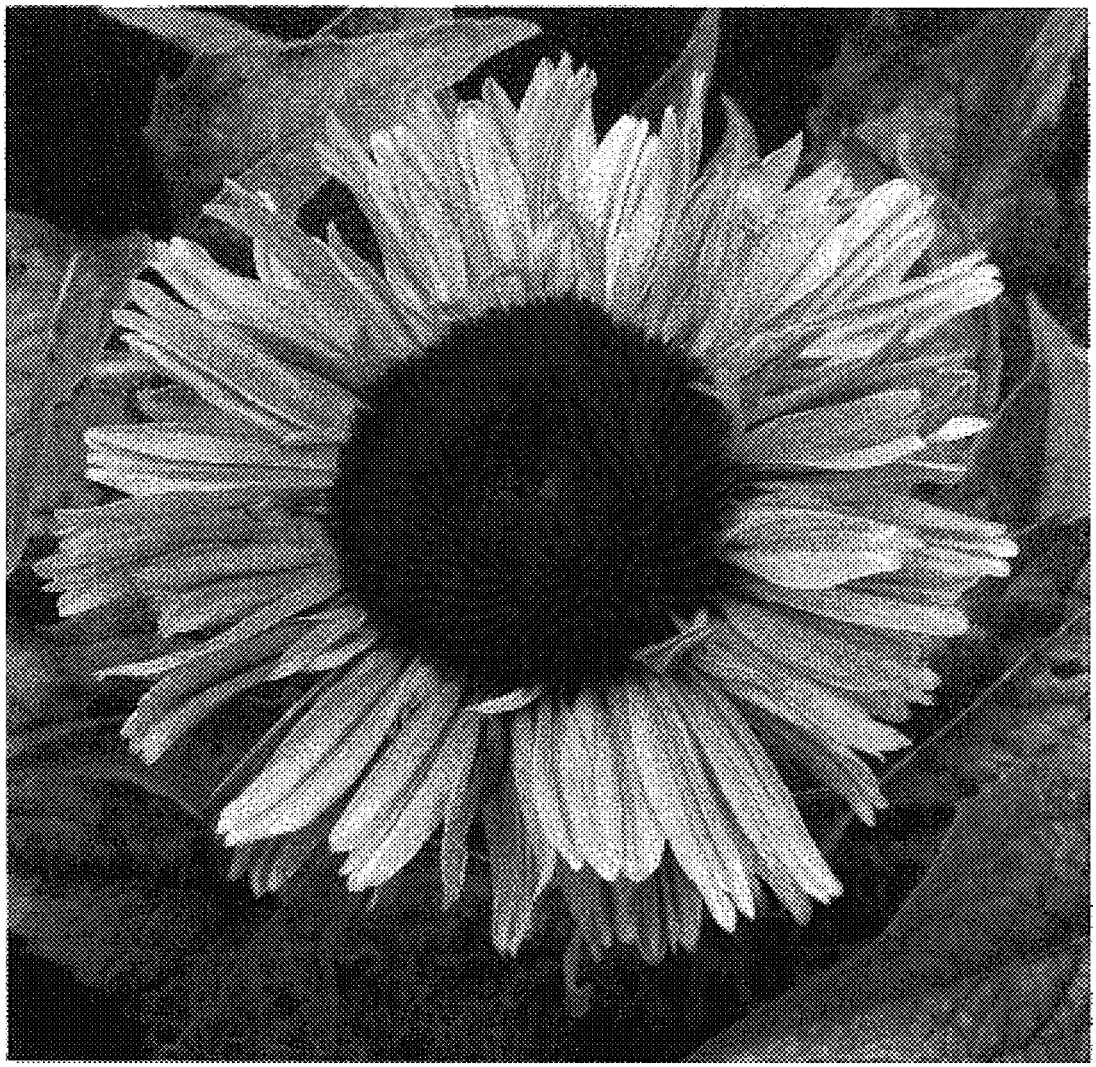

* * * * *